United States Patent [19]

Pottenger et al.

[11] Patent Number: 5,387,240
[45] Date of Patent: Feb. 7, 1995

[54] FLOATING BEARING PROSTHETIC KNEE

[75] Inventors: Lawrence Pottenger; Louis F. Draganich, both of Chicago, Ill.

[73] Assignee: Arch Development Corporation, Chicago, Ill.

[21] Appl. No.: 976,803

[22] Filed: Nov. 16, 1992

Related U.S. Application Data

[63] Continuation-in-part of Ser. No. 613,331, Nov. 14, 1990, abandoned.

[51] Int. Cl.$^6$ ............................................... A61F 2/38
[52] U.S. Cl. .......................................... 623/20; 623/18
[58] Field of Search ........................ 623/18, 19, 20, 21

[56] References Cited

U.S. PATENT DOCUMENTS

| | | | |
|---|---|---|---|
| 4,728,332 | 3/1988 | Albrektsson | 623/20 |
| 4,888,021 | 12/1989 | Forte et al. | 623/20 |
| 4,892,547 | 1/1990 | Brown | 623/20 |

FOREIGN PATENT DOCUMENTS 0346183 12/1989 European Pat. Off. ............ 623/20

*Primary Examiner*—David Isabella
*Assistant Examiner*—Debra S. Brittingham
*Attorney, Agent, or Firm*—McDermott, Will & Emery

[57] ABSTRACT

A semiconstrained prosthetic knee for surgical replacement of a dysfunctional knee includes a tibial platform, a movable bearing element, and a femoral component. The femoral and tibial components are typically constructed of a cobalt-chromium alloy and each includes an extension for securing the component to the bone. The femoral component includes a polycentric convex bearing which slidably engages a movable bearing, typically constructed of high molecular weight polyethylene. The superior surface of the bearing element is designed to congruently slidably engage the inferior surface of the bearing portion of the femoral component throughout the flexion/extension range of the knee. The inferior surface of the femoral component is generally convex with two or more offset portions of varying radii of curvature matching complimentary superior surfaces of the bearing element. The inferior surface of the femoral component may have more than one radii of curvature at different points along the convex surface. The superior surface of the tibial platform is generally flat and includes at least one protrusion for controlling the movement of the bearing element.

26 Claims, 4 Drawing Sheets

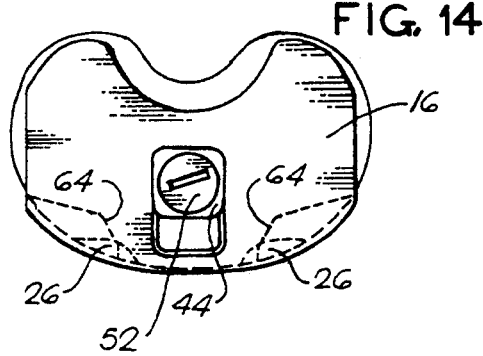
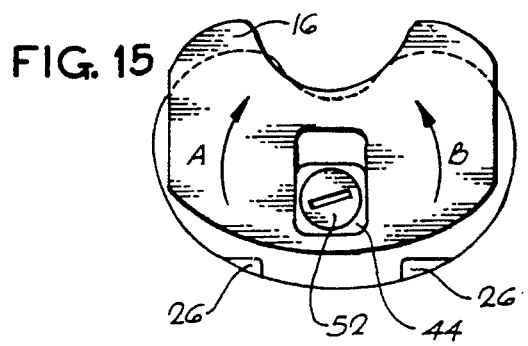
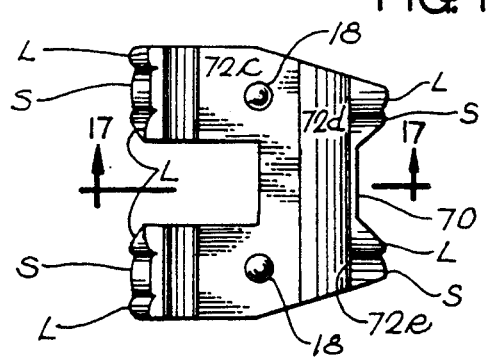
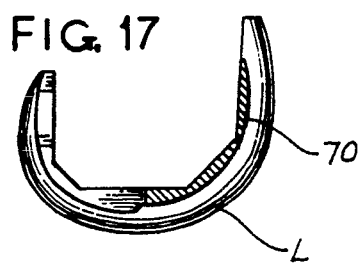
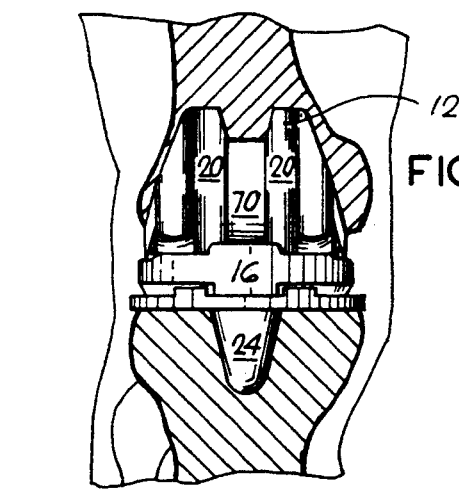
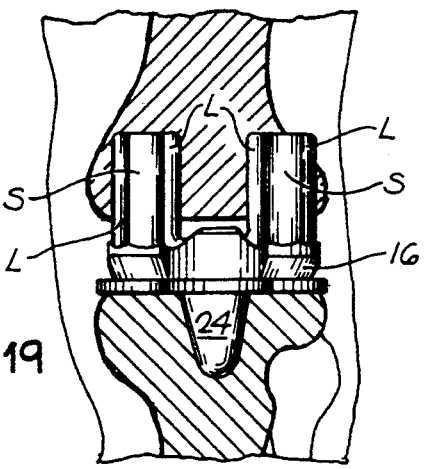
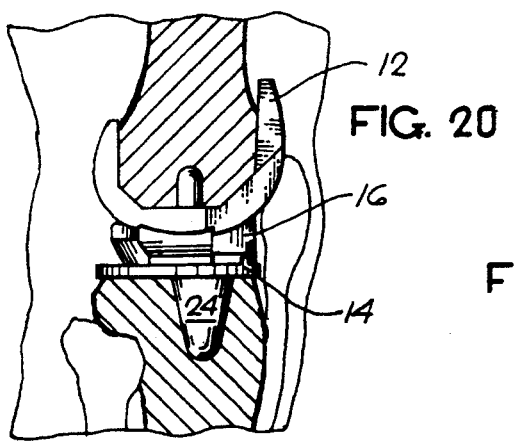
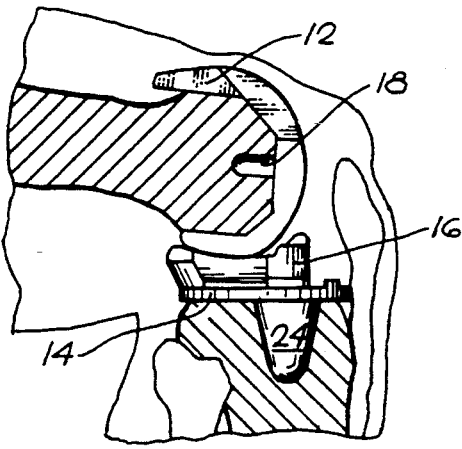

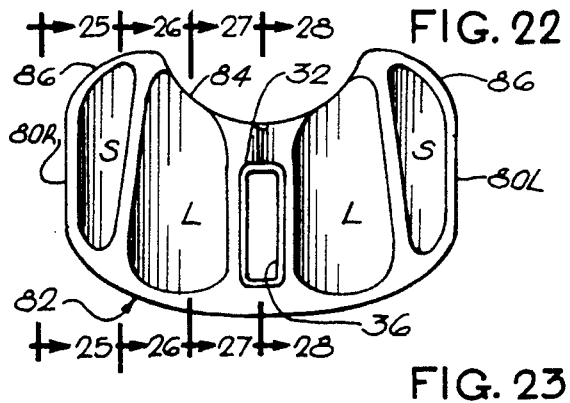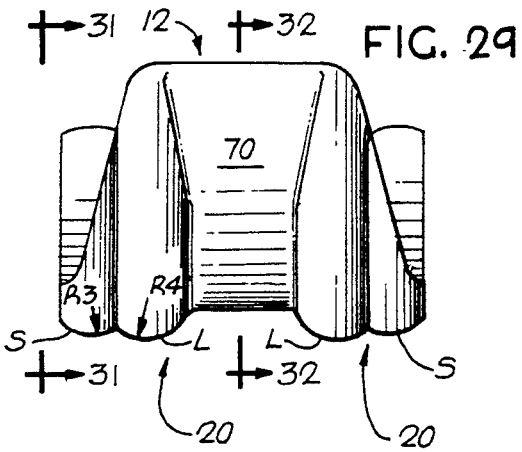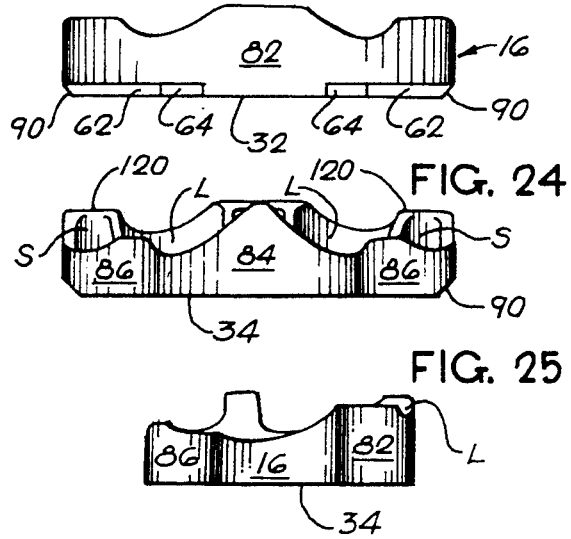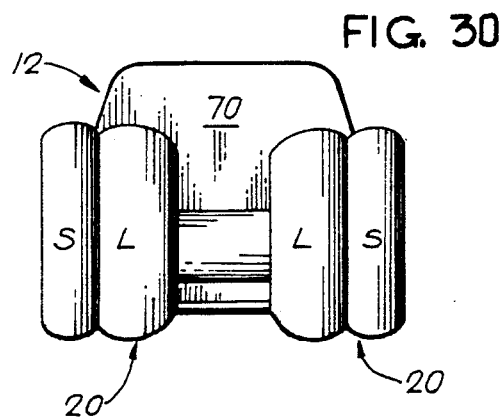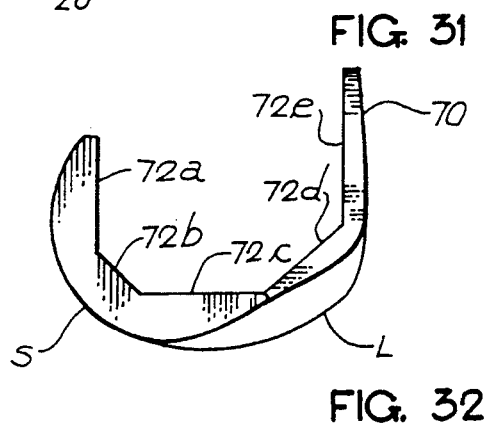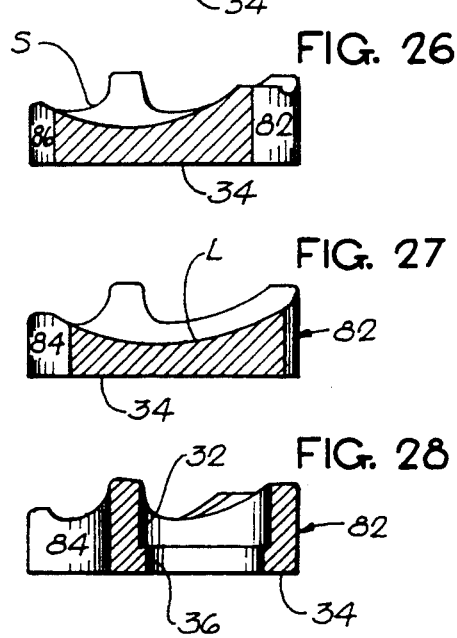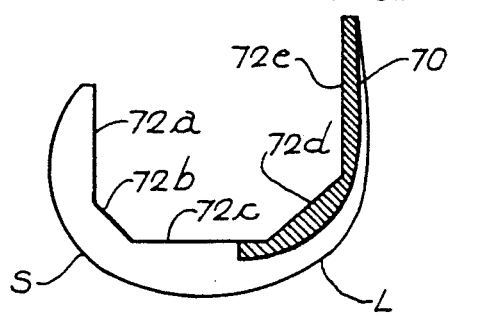

FLOATING BEARING PROSTHETIC KNEE

This is a continuation-in-part of application Ser. No. 07/613,331, filed on Nov. 14, 1990 now abandoned.

BACKGROUND OF THE INVENTION

1. Field of the Invention

This invention relates to prosthetic joints generally, and more particularly to an improved, unconstrained prosthetic knee replacement for a dysfunctional knee.

2. Prior Art

Referring now to prior art knee endoprostheses, there are basically two types of prosthetic replacement knees known generally as constrained and unconstrained knees. An example of an unconstrained or floating meniscal bearing knee is disclosed in Buechel et al U.S. Pat. No. 4,340,978. An embodiment of the Buechle invention is manufactured and sold by Depuy, Inc. of Wausau, Ind. Preferably, the bearing elements of these types of knees are manufactured with high density polyethylene such as that disclosed in Zachariades U.S. Pat. No. 4,587,163 developed by Polteco Inc. of Alameda, Calif. because of its superior wear resistant characteristics. Both classes of prior art prosthetic knees have had problems often resulting in failures requiring additional surgery and repair or reconstruction.

Referring next to typical prior art tibial-femoral knee prostheses, prostheses which allow axial rotation and A-P motion in addition to flexion-extension motion have incongruent contact (usually theoretical point-contact) between the femoral and tibial bearing surfaces, have been found to produce excessive contact stresses leading to deformation and/or early wear and undesirably short prosthetic life. Also, wear products have been shown to produce undesirable tissue reactions which may contribute to loosening of the prosthetic components.

Those prior art knee prostheses which do provide congruent or area bearing contact fail to provide the needed axial rotation, or when cruciates are present the needed anterior-posterior motion. This lack of axial rotation and anterior-posterior motion has been found clinically and experimentally to result in deformation and loosening of the tibial components, and such prostheses now appear to be falling into disuse.

Pre-existing constrained knees have often resulted in early failure as a result of hinge constrainment. The degree of rotation was limited to either only one plane or a very small arc causing a loosening and failure of the connection points between the prosthesis and the tibia or femur. Also, as shown in U.S. Pat. No. 4,219,893, very little flexibility was possible in the shape of the patello-femoral interfaces because of the requirement to maintain congruent patello-femoral contact over the range of motion of the knee. As a result, patello-femoral tracking problems became commonplace.

It was necessary to use a large circumference when used to resurface allografts resulting in problems with soft tissue necrosis and/or patello-femoral tracking problems as described above. Furthermore, most implants were known as custom devices since they had to be specially made to fit a particular patient's size and thus required excess manufacturing time and unnecessary delays.

An additional, significant problem with prior art constrained knees results from the fact that the range of motion prevents the normal A-P movement of the inferior end of the femur relative to the posterior end of the tibia. This "sliding" movement is necessary in order to maintain the full range of motion desired in a prosthetic device.

Current prostheses of the dislocatable cruciate retaining type, such as the Geomedic knee replacement shown in U.S. Pat. No. 3,728,742 to Averill et al, that produce area contact provide only one axis of rotation relative to the femur for the flexion-extension motion. Normal flexion-extension is, however, characterized by a polycentric flexion-extension motion where rotation relative to the femur occurs about many axes.

This polycentric motion, which results from the action of the cruciate ligaments and condylar shape, allows for more efficient utilization of muscle forces by providing a posterior shift of the axis when effective quadriceps action is important and an anterior shift when hamstrings effectiveness is important. Furthermore, in the human knee it is this action and the A-P shift, and the shape of the posterior condyles, which influence this motion so as to allow full flexion capability for the knee. Failure to provide appropriate knee geometry inhibits, when cruciate ligaments are present, this natural motion and thus tends to restrict muscle effectiveness and inhibit flexion. These restrictions tend to increase both loading on the prosthesis (which increases wear or likelihood of deformation or breakage) and loading between prosthesis and bone (which increases the possibility of component loosening).

It has been found that loosening problems result from the direct attachment of plastic prosthetic components to bone through the use of relatively brittle cement that is weak in tension. Specifically, it has been demonstrated that even relatively thick plastic components when loaded in a normal fashion produce undesirable tensile stresses in the acrylic cement commonly used to secure such plastic components to bone. Such loading tends to produce bending of the plastic component which causes the ends of the plastic component to lift away from the bone, thereby subjecting the bone-cement attachment to tension. As is known, cement has very poor tensile fatigue properties. The bone to which the plastic prosthesis is cemented also appears to be adversely affected by tensile loads. Accordingly, these combined effects contribute substantially to prosthetic loosening problems and, specifically, it has been noted where clinical failure due to loosening occurs in a knee prosthesis that is almost always the plastic prosthesis component which loosens.

Another prior art prosthesis problem exists with regard to knee endoprostheses for implantation in those cases wherein the cruciate ligaments are functionally absent but where the collateral ligaments are functional or at least reconstructable. In the absence of cruciate ligaments, the prosthetic replacement must provide anterior-posterior knee joint stability so as to replace that stability otherwise provided by the cruciates. Until recently most such cases were treated by a constrained type knee prosthesis which may suffer from the loosening problems described above caused by the stresses described above. Necrosis of the bone, caused by altered mechanical bone stresses, is also a problem with the prior art constrained knee prostheses.

Where the cruciate ligaments are present, most surgeons would prefer their retention, since they provide important internal stabilizers and, together with the condylar geometry of the femur and tibia, control the rotation axis and A-P motion of the knee. Furthermore, these ligaments provide anterior-posterior stability. Thus, it is desirable to reserve the cruciate ligaments, even though reasonable stability can be provided by a properly designed full platform type prosthesis.

In addition, the action of the cruciate ligaments produces a shift in the rotation axis of the knee which results in more efficient muscle utilization. Thus, preservation of these structures provides better physiological function after knee replacement.

It is not, however, clear that the physiological advantages gained in retaining the cruciates outweigh the disadvantages of the design compromises, such as increased bearing surface incongruency and reduced tibial prosthesis bearing area, required to retain these ligaments. Thus, the desirability of retaining the cruciate ligaments in the cases of unconstrained knee replacement is not well established.

A recent unconstrained knee concept, the New Jersey knee, appears to provide a partial solution to the problem of overconstraint while attempting to maintain congruency by the use of mensical floating elements. Unfortunately, this knee suffers from several design problems which appear to limit its usefulness.

The present invention, the Pottenger/Draganich Knee utilizes new concepts combined in an improved design in order to avoid some of the anticipated difficulties of the prior art design.

SUMMARY OF THE INVENTION

The present invention is directed to an improved prosthesis for the replacement of all or a portion of a dysfunctional human knee joint.

An object of the present invention is to provide an improved semiconstrained knee prosthesis with a novel polycentric femoral component having different radii of curvature in different sagittal sections.

An object of the present invention is to provide a knee prosthesis which facilitates rotation about one or more axes in the presence of congruency of the bearing surfaces.

A further object of the present invention is to provide a knee prosthesis which substantially reduces the possibility of tipping and/or dislocation of the bearing insert or inserts in the absence of the anterior and posterior cruciate ligaments.

A further object of the present invention is to provide a knee prosthesis which allows full flexion of the reconstructed knee without applying shear forces.

A further object of the present invention is to provide a knee prosthesis where the tibiofemoral area contact controls the movement of the femoral component and thus increases quadriceps effectiveness.

An object of the present invention is to provide a knee prosthesis in which A-P sliding of the bearing element with knee flexion allows the normal anatomical shift in the center of the area of contact between femoral and tibial condyles.

A further object of the present invention is to provide a knee prosthesis with improved medial-lateral stability, substantially unaffected by axial rotation or anterior-posterior (A-P) shift of the bearing element.

A further object of the present invention is to provide a knee prosthesis which includes constraints at the limits of normal motion to compensate for missing cruciate ligaments and prevent dislocation.

A further object of the present invention is to provide a semiconstrained knee prosthesis where the femoral component may articulate in extremely close proximity with the tibia to eliminate patella baha problems.

In accordance with the foregoing and other objects, the unconstrained prosthetic knee of the present invention includes a femoral prosthesis having a pair of condylar portions, each having, preferably two saggitally spaced arcuate segments of different radii, a tibial prosthesis having a bearing surface for supporting weight, and an intermediate load-bearing member having a thrust-bearing surface for matingly engaging the bearing surface of the tibial prosthesis and adapted to distribute weight and to transmit forces in a plane substantially perpendicular to the axis of the tibia and a mutually congruent superior surface for engaging the condyles of the femoral prosthesis to provide area contact throughout the full range of flexion/extension of the knee.

BRIEF DESCRIPTION OF THE DRAWINGS

A complete understanding of the invention may be obtained from the detailed description which follows, together with the accompanying drawings, wherein:

FIG. 14 is a diagrammatic representation of the assembled bearing element and tibia portion showing the bearing element in its forwardmost position;

FIG. 15 is a diagrammatic representation similar to FIG. 14 showing the bearing element in its rearwardmost position;

FIG. 16 is a top plan view of the femoral component on a reduced scale;

FIG. 17 is a vertical section taken generally along the line 17—17 of FIG. 16;

FIG. 18 is a front elevational view of the prosthesis assembly of FIG. 1 implanted within a patient;

FIG. 19 is a rear elevational view of the prosthesis assembly of FIG. 1 implanted within a patient;

FIG. 20 is a side elevational view of the prosthesis assembly of FIG. 1 in a generally, straight extended position;

FIG. 21 is a diagrammatic representation of the prosthesis assembly of FIG. 1 with the knee shown in flexion.

FIG. 22 is a top plan view of the bearing element made in accordance with the preferred embodiment of the present invention;

FIG. 23 is a front elevational view of the bearing element of FIG. 22;

FIG. 24 is a rear elevational view of the bearing element of FIG. 22;

FIG. 25 is a side elevational view taken along the line 25—25 of FIG. 22;

FIG. 26 is a vertical section taken generally along the line 26—26 of FIG. 22;

FIG. 27 is a vertical section taken generally along the line 27—27 of FIG. 22;

FIG. 28 is a mid-vertical section taken generally along the line 28—28 of FIG. 22;

FIG. 29 is a front elevational view of the femoral component of the preferred embodiment.

FIG. 30 is a bottom plan view of the femoral component of the preferred embodiment;

FIG. 31 is a side elevational view of the femoral component taken generally along the line 31—31 of FIG. 29; and FIG. 32 is a mid-vertical section of the femoral component taken generally along the line 32—32 of FIG. 29.

BRIEF DESCRIPTION OF THE PREFERRED EMBODIMENT

The prosthetic knee of the present invention is shown and described herein with respect to two embodiments. The two embodiments differ in the number of arcuate surfaces provided for sliding engagement between the femoral component and the bearing element as described in detail hereinafter. The embodiment shown and described in FIGS. 1-21 describe the prosthetic knee design utilizing three arcuate surfaces on each of the condyls of the tibial component. The preferred embodiment, shown in FIGS. 22-32 utilizes only two arcuate surfaces for the improved knee as shown and described in detail herein. For convenience, the same numerals are used to describe the same element in the respective embodiments.

Figure 1:
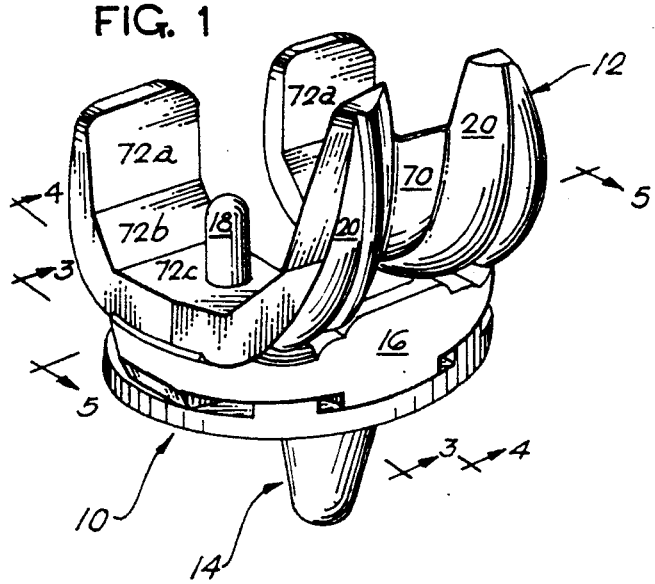
FIG. 1 is a perspective view of one embodiment of the unconstrained prosthetic knee of the present invention.

The floating bearing prosthetic knee, generally designated 10 in FIG. 1, provides area contact as opposed to line contact or point contact throughout the entire flexion/extension range of the prosthesis. Through this design, some degree of rollback automatically occurs as the knee flexes and additional rollback is allowed to will occur through the movement of the sliding bearing. Area contact throughout the full range of motion is obtained through the use of multiple arcuate sections along the path of conduct of the condyles with the bearing insert. However, unlike prior art prosthetic knees of the prior art, the different radii and arcuate portions of the condyles lie in different saggital or medial-lateral planes. Thus tibial-femoral area contact will occur in different longitudinal planes throughout the flexion/extension range of the knee. Area contact will occur simultaneously in two planes only at the point of transition between the respective arcuate portions.

The desirable prosthetic knee 10 satisfies at least five characteristics. One, the knee should have the normal polycentric motion of the normal knee joint. Two, unconstrained anterior-posterior motion and rotation would be permitted within the normal range of motion of the knee. Three, constrained A-P motion and rotation would occur at the limits of normal motion. Four, normal rollback of the femur with respect to the tibia should occur during flexion of the knee. Five, tibial-femoral contact pressure should be minimized in order to reduce wear on the polyethylene bearing insert 16. The present invention 10 satisfies these five characteristics as described hereinafter.

MAJOR COMPONENTS

Referring now in particular to FIG. 1, the unconstrained knee, generally designated 10, is shown in perspective view to include a femoral component 12, a tibial component 14, and a bearing element 16. The femoral component 12 includes at least one upwardly extending stem 18 or other means for connection to the femur and a pair of condyles 20 on its inferior surface for engagement with the bearing portion 16. Preferably, the bearing element 16 is constructed of a tough, wear-resistant, resilient material such as high density polyethylene. The remaining elements of the prosthetic knee are metallic and preferably manufactured of a cobalt-chromium alloy material approved for use in prosthetic devices.

THE TIBIAL COMPONENT

The tibial component includes a generally flat rigid platform 22 and a depending stem portion 24 for securing the tibial portion to the tibia. The superior surface of the femoral component and the implantable stem portion 24 and inferior surface of the platform 22 of the tibial component include a surface adapted for extramedullary porous ingrowth to secure the prosthetic device within the tibia and femur, respectively, of the host or allograph bone of the patient. By contrast, the condyles 20 of the femoral component are highly polished to reduce friction.

Figure 2:
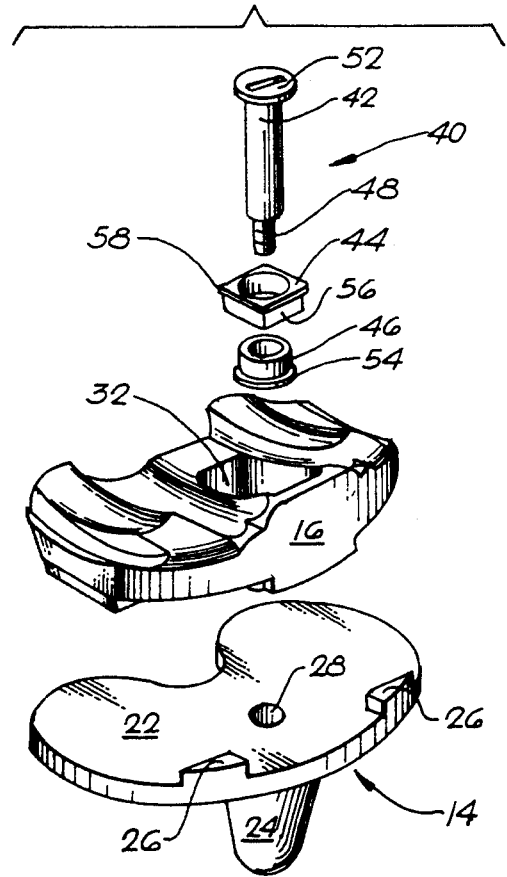
FIG. 2 is an exploded perspective view of the tibial component and bearing element of the prosthetic knee of FIG. 1.

Referring to the lower portion of FIG. 2, the tibial portion includes the platform 22 and the depending stem 24. The platform is provided with a pair of laterally spaced, generally triangular-shaped, upward protrusions 26 and a centrally located aperture 28 for limiting the A-P movement of the bearing 16 described below.

Figure 5:
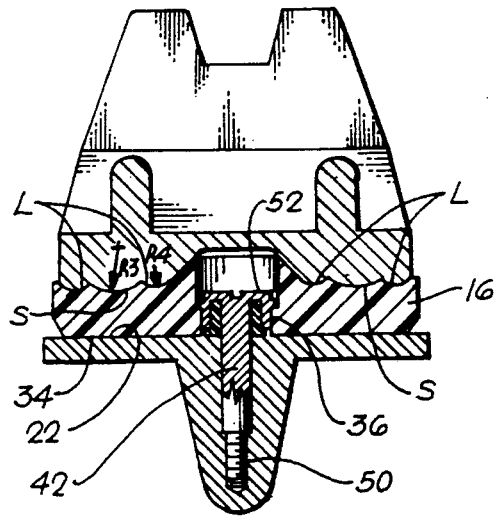
FIG. 5 is a vertical section taken generally along the line 5—5 of FIG. 1.
Figure 6:
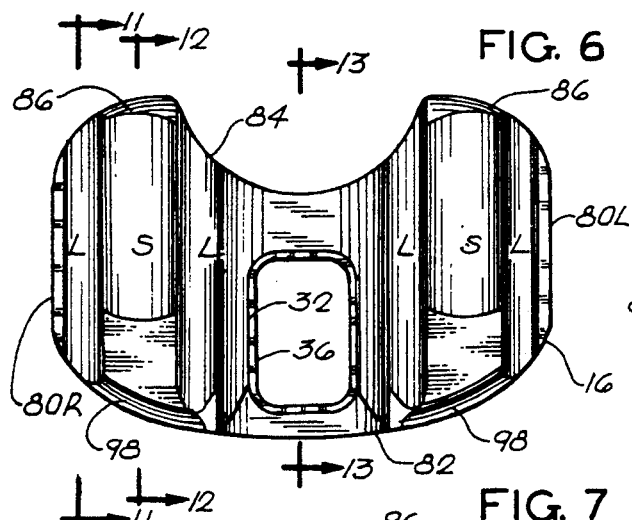
FIG. 6 is a top plan view of the bearing element made in accordance with the present invention as shown in FIG. 1.
Figure 10:
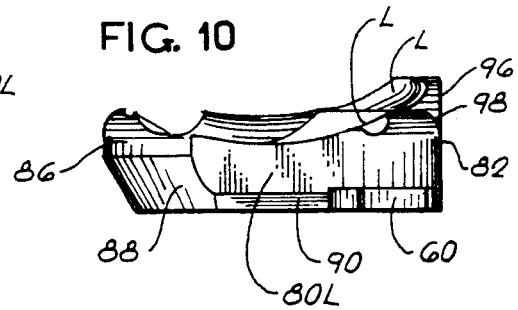
FIG. 10 is a side elevational view of the bearing element of FIG. 6.
Figure 7:
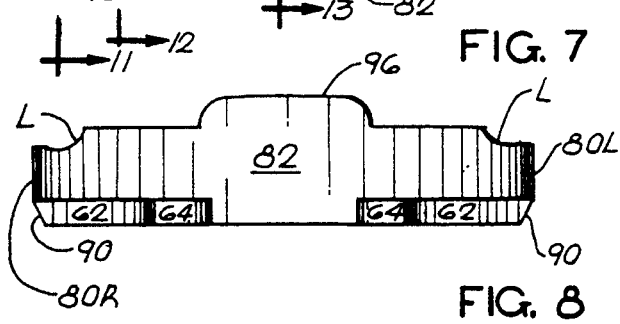
FIG. 7 is a front elevational view of the bearing element of FIG. 6.
Figure 11:
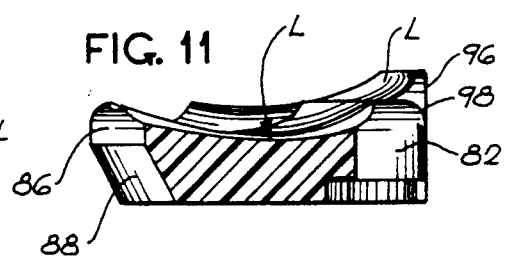
FIG. 11 is a vertical section taken generally along the line 11—11 of FIG. 6.
Figure 8:
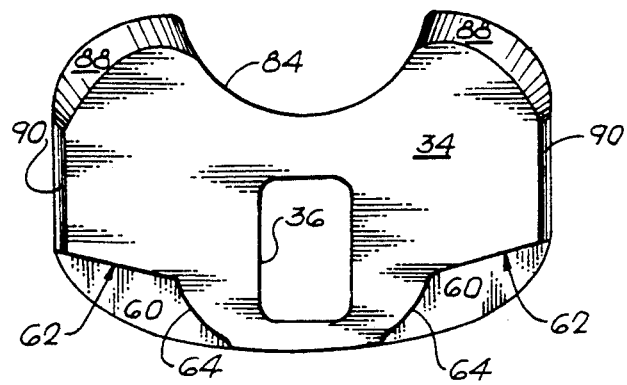
FIG. 8 is a bottom view of the bearing element of FIG. 6.

More particularly, referring to FIGS. 2, 5 and 6, the bearing 16 includes a centrally located generally rectangular opening 32 which is used to slidably connect the bearing to the top of the tibial component 22. The bearing 16 has a generally flat inferior surface 34 as shown in FIG. 8 which slidably engages the superior surface or platform 22. The aperture 32 includes, at its lower end, a ridge or lip 36, of similar configuration. Both the aperture 32 and the vertical wall of the bearing have smooth or rounded corners to reduce stress. The bearing 16 is captured by a retaining means, generally designated 40, which includes a shoulder bolt 42, a retainer 44 and a spacer 46. The spacer 46 and retainer 44 are preferably manufactured of high density polypropylene, similar to that used for the bearing insert 16 and the shoulder bolt 42 would be made of stainless steel or cobalt-chromium alloy approved for use in this application.

The shoulder bolt 42 includes a lower threaded portion 48 which engages a plurality of threads 50 at the lowermost end of the aperture 28 within the stem 24 of the tibial component. The shoulder sets the depth to prevent from the head 52 of the shoulder bolt from impeding the movement of the bearing insert 16. The retainer 46 includes an enlarged diameter ring 54 at its lowermost end which engages the platform 22 of the tibial portion 14 around the aperture 28 and extends upwardly coaxially with the shoulder bolt 42.

The retainer or retaining element 44 is generally square in shape and includes a lower square portion 56 which forms a clearance fit within the ridge 36 at the lower end of the aperture 32 in the bearing, as can be seen in FIG. 5. The upper end of the retainer includes an enlarged flange 58 which engages the top of the step or lip 36. The retainer 44 is dimensioned so that the distance between the underside of the head 52 of the shoulder bolt and the top of the lip 36 provides a low tolerance clearance fit with the flange 58 of the retainer to allow the bearing 16 to slidably move on the platform 22 without becoming disengaged from the platform 22. In this manner, the bearing is free to slide in an anterior posterior or A-P path. The retainer 44 will stop the movement in the A-P direction as the front and rear surfaces engage the front or inner surfaces of the lip 36.

The retaining means 40, in addition to permitting A-P movement of the bearing 16 also permits pivotal movement generally about the center line of the shoulder bolt 42. Thus, depending upon the anterior or posterior displacement of the bearing insert 16 relative to the retainer 44, the bearing insert and the retainer may pivot about the center line of the shoulder bolt 42 to provide freedom of movement. However, in order to prevent too much pivotal movement of the bearing 16, particularly when in its anteriormost position, the triangular protrusions 26 provide a stop means.

Figure 4:
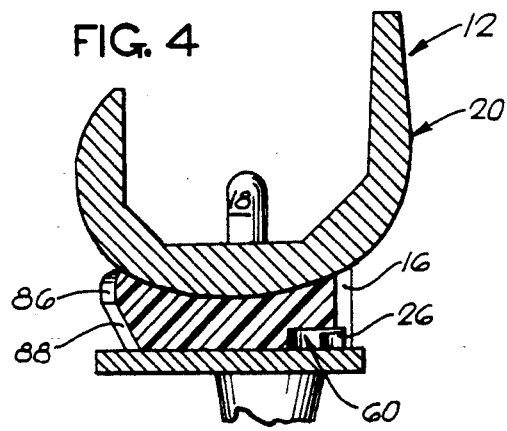
FIG. 4 is a vertical section taken generally along the line 4—4 of FIG. 1.

The stop means includes the upward protrusions 26 and a pair of symmetrical cutouts 60 on the lower surface of the bearing insert 16. In particular, each cutout includes a generally flat rear wall 62 and a generally curved inner wall 64 for engagement with the upward protrusions 26. As shown in FIG. 4, the height of the rear wall 62 permits the cutouts 60 to clear the top of the stops 26. Referring to FIG. 14, in its anterior-most position, the arcuate walls 64 of the bearing 16 engage the inner, generally right angle corner of the triangular protrusions 26 to virtually preclude most of the pivotal movement or rotational movement of the bearing insert 16. As the bearing 16 is moved towards its posteriormost position, as shown in FIG. 15, the bearing is free to rotate in either direction as shown by arrows A and B and are limited by the longer upstanding walls of the protrusions 26 which engage the flat walls 62 within the cutout 60.

Therefore, it can be seen that the bearing insert 16 is constrained but is permitted to move in the A-P direction from the extremes as shown in FIG. 14 to that as shown in FIG. 16 while, at the same time, it is free to pivot about an axis defined by the shoulder bolt 24 within the limits created by the stop means where the walls 62 and 64 of the cutouts 60 engage the triangular protrusions 26. These constraints, while permitting movement of the bearing 16, control the movement of the femoral component as described hereinafter and thus create some rollback and allow for the further posterior movement of the bearing insert.

These constraints at the limits of normal motion will compensate for missing cruciate ligaments and prevent dislocation of the components, i.e., the bearing insert, which has been seen to occur in popular prior art floating bearing prosthetic knees. In most circumstances, normal soft tissue will provide the primary restraining forces limiting motion of the components and, if necessary, the limits incorporated into the prosthesis 10 would function as secondary restraints.

Some rollback (approximately 5 millimeters in the present embodiment) automatically occurs (i.e., is obligated to occur) when tibiofemoral contact moves from one arcuate segment to the other one. The rest of the normal amount of rollback is allowed to occur (but not obligated to occur) with the movement of the bearing insert. The amount of additional rollback that is allowed to occur is governed by the interaction of the posterior cruciate ligament and the condylar surfaces. The rollback of the femur with respect to the tibia during flexion of the knee is an important characteristic of the present prosthesis because it causes the patellar tendon to move anteriorly with respect to the femur which greatly increases the effectiveness of the quadriceps muscle, especially when rising from a chair. It has been found that many patients who have had total knee replacements cannot get up from a sitting position without assistance from their arms. Also, prior art unconstrained knees are frequently found to "roll forward" rather than backward during flexion. In the design of the present invention, the shoulder bolt retaining means 40 prevents roll forward and the bearing insert 16 recreates the normal situation and further helps to increase the quadriceps efficiency. Known prior art total knee replacements have attempted to utilize the femoral component to control the motion of the bearing insert, just the opposite of the knee of the present invention.

THE FEMORAL COMPONENT

The femoral component 12 of the present invention includes generally a pair of condyles 20, securing posts 18 and a web portion which defines a patella track 70. The securing posts 18 provide means to secure the femoral component to the femur of a patient. As shown in FIG. 20, a pair of matched apertures are drilled into the femur and the end of the femur is formed with five generally flat surfaces as shown to fit within the flat surfaces 72a through 72e as shown. The opposite surfaces 72a and 72e are generally parallel to one another and perpendicular to the surface 72c. The angled surfaces 72b and 72d are approximately at 45 degrees with respect thereto. The entire surface of the flat surfaces 72a–e and the surfaces of the posts 18 are designed for extramedullary bone growth to secure the femoral component to the end of the femur.

Certain prior art prostheses propose the use of a femoral component in which the multicentric surfaces of the condyles were created by a common planar curve which created a design whereby every sagittal section along the condyle was polycentric. This design results in a situation where the condyles can only make area contact during approximately the initial 20° of knee flexion thereby resulting in line contact and very high contact pressure which increases the wear of the bearing insert. In addition, prior art design of this type accommodates rollback of the femur with respect to the tibia and, particularly at maximum flexion, there is a tendency for the bearing insert to "pop out" or become dislocated.

The femoral component and sliding bearing of the present invention have congruent surfaces which allows for rotation and A-P motion within the range of normal A-P motion to prevent excessive anterior and posterior drawer and rotation and dislocation of the bearing. The upper surface of the bearing 16 is designed so that the inferior surfaces of the femoral component always have area contact at all flexion angles. Constant area contact is achieved by distributing the femoral contact areas on the bearing 16 across the frontal plane such that different areas of the bearing 16 are contacted through different angles of knee flexion. Each contact area on the bearing has the same radius of curvature as the portion of the inferior surface of the femoral component 12 in contact with the bearing.

THE BEARING INSERT

Referring to FIGS. 6–13, the bearing insert 16 is generally oval in shape with a pair of flat ends 80R and 80L. The anterior or front side is a generally flat arcuate wall 82 which includes a pair of cutouts 60 at the lower right and left ends, respectively. The posterior side includes a relatively large, almost semicircular recess 84 which provides substantial clearance for the posterior cruciate ligaments. The top portion of the rear wall on either side of the recess 84 includes a short generally vertical arcuate wall portion 86 which merges into a generally arcuate, inwardly tapered lower wall portion 88. The tapered portions 88 merge with a pair of lower champhers at the bottom of the end walls 80R and 80L which terminate at their front ends with the cutouts 60.

The superior surface of the bearing insert is described by a plurality of arcuate channels or grooves which are described in detail hereinafter in connection with the arcuate surfaces defined on the inferior contact surface of the femoral component. In order to add rigidity to the front wall portion 82, an upstanding flange 96 is included immediately anteriorly of the aperture 32. The outer edges of the top of the front wall 82 are softened by curves 98 as the transition to the top of the bearing insert 16.

CONTACT SURFACES

Figure 12:
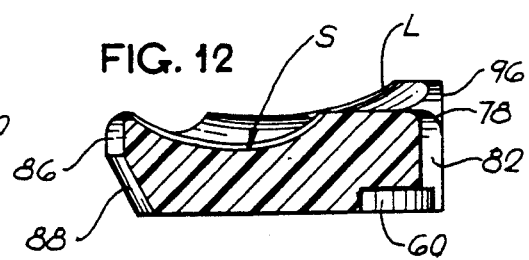
FIG. 12 is a vertical section taken generally along the line 12—12 of FIG. 6.
Figure 9:
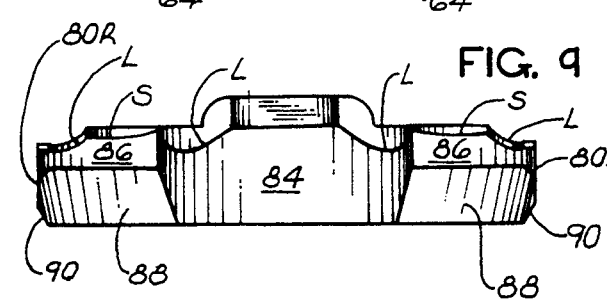
FIG. 9 is a rear elevational view of the bearing element of FIG. 6.
Figure 13:
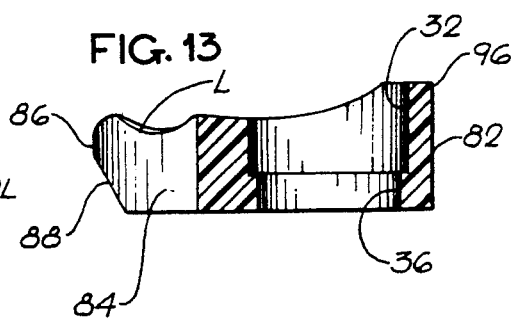
FIG. 13 is another vertical section taken generally along the line 13—13 of FIG. 6.

The contact surfaces between the bearing insert 16 and the femoral component 12 are best understood if considered together. The upper surface of the bearing 16 includes a plurality of arcuate surfaces for engagement with congruent arcuate surfaces on the inferior side of the femoral component 12. Referring to FIG. 6, four of the arcuate surfaces have been labelled L and two of the surfaces have been labelled S. The four arcuate surfaces L are all generated using the same radius of curvature and similarly the two arcuate surfaces labelled S are generated using the same but smaller radius. The arcuate surface S shown in section view in FIG. 12 is defined posteriorly of the arcuate surfaces L, one of which is shown in sectional view in FIG. 11. As can be seen in FIG. 5, the complementary surface of the femoral component includes four arcuate surfaces L and two arcuate surfaces S. One significant feature of the present invention is that the arcuate surfaces L and R lie in different saggital planes as shown and make contact during different degrees of flexion of the knee.

In particular, the arcuate surfaces L on the inferior surface of the femoral component are in contact with the arcuate surfaces L on the bearing 16 between approximately 0° through 8° of flexion of the knee and the arcuate surfaces S of the femoral component are in contact with the arcuate surfaces S of the bearing 16 during approximately 8° through 140° of flexion of the knee. At the transition point, at approximately 8° of flexion, area contact occurs between all of the arcuate surfaces L and S on the femoral component 12 with all of the arcuate surfaces L and S on the bearing component 16.

Although the size of the patient will partially determine the size of the prosthesis, the following sizes have been found to be effective in trials. More particularly, referring to FIG. 3, the arcuate surfaces L are generated by radius R1 about a center point C. Center point C is slightly rearwardly defined relative to the post 18 and the radius R1 is approximately 1.60". The arcuate surfaces S are generated by a radius R2 about a center of rotation D. The radius R2 is approximately 0.75". The center of rotation D of radius R2 lies on a line passing through the center of rotation C of R1 so that the surfaces L and R have a tangent point T in order to have a smooth transition of tibia-femoral contact at approximately 8° of flexion. Thus, area contact of the arcuate surfaces L occurs during the first 8° of flexion of the knee and area contact is transferred to the arcuate sections S at approximately 8° and continues through maximum flexion of about 140°.

The position of the femoral component 12 with regard to the bearing 16 is controlled by the center of rotation of curvature for the arcuate surfaces S or L which are in contact. The arcuate curves S are placed farther back on the bearing and will draw the femoral component posteriorly thus allowing obligatory rollback. Further rollback is permitted because the elongated aperture 32 in the bearing allows the bearing to move posteriorly on the tibial platform. As described previously, the constraints 26 and the retaining means 40 prevent anterior movement of the bearing 16 beyond the anterior edge of the tibial component. Therefore, when rollback is occurring during flexion of the knee, no compensatory roll forward will occur between the bearing 16 and the tibial component 14. As the femoral component passes through approximately the 8° range, area contact is transferred between the arcuate surfaces L to the arcuate surfaces S, the transition continues smoothly because of the common tangent point of the respective arcuate surfaces. The constraints as previously described with respect to the bearing 16 prevent dislocation of the bearing element when implanted.

In an alternative embodiment, it is possible to obtain the same functionality and operation if, for example, the innermost or outermost complementary arcuate surfaces L were eliminated. However, additional area contact can be obtained to decrease the pressure between the femoral component and the bearing by providing the additional arcuate surfaces L adjacent the center aperture 32.

In addition, the arcuate surfaces L and S are designed to obtain the maximum amount of area contact possible within the permissible space. To this end, the arcuate surfaces S on the bearing 16 are approximately $\frac{3}{8}$" wide and approximately $1\frac{1}{8}$" long. As described previously, the radius R2, the radius for generating the arcuate surface S is approximately 0.75" and lies in a sagittal plane. The transverse radius which defines the arcuate surface in the medial lateral plane as shown in FIG. 5 is approximately 0.375". Similarly, the arcuate surfaces L are approximately 1.25" in length generated by the radius R1 in the sagittal plane and the radius in the transverse plane R4 (FIG. 5) which defines a radius of curvature of the arcuate surfaces L in the transverse plane is approximately 0.125". The center of rotation D is approximately 0.375" posteriorly of the center of rotation C and about 0.9" below the center of rotation C. The center lines of the arcuate surfaces L are approximately 0.3" on either side of the center line of the arcuate section S and the respective center lines of the arcuate sections S are approximately 2.00″ apart.

FIGS. 22–32 describe the preferred embodiment of the present invention, which as described previously, is simpler in design and provides better performance. The preferred embodiment differs in several respects but primarily in the number of arcuate surfaces in contact between the femoral component 12 and the bearing surface 16. In particular, this embodiment uses two arcuate surfaces on either side of the midline of the femoral component and the bearing surface as to the design which includes three arcuate surfaces described previously with respect to the embodiment shown in FIGS. 1–21.

Figure 3:
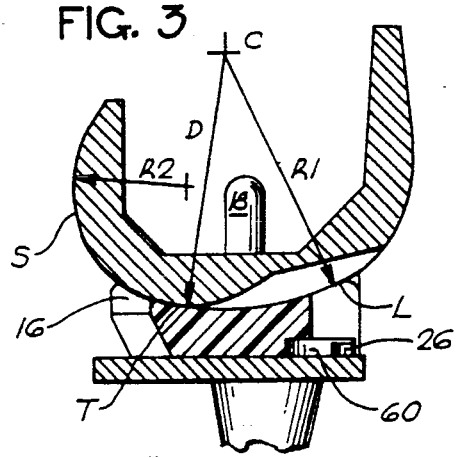
FIG. 3 is a vertical section taken generally along the line 3—3 of FIG. 1.

Referring to FIG. 29, the femoral component includes a pair of condyls 20 each of which includes two arcuate surfaces L and S. In particular, the arcuate surfaces L on the inferior surface of the femoral component are in contact with congruent arcuate surfaces L on the bearing element 16 between approximately 0 and 8° of flexion of the knee. The arcuate surfaces F of the femoral component are in contact with the arcuate surfaces S of the bearing element 16 during approximately 8° through 140° of flexion of the knee. At the transition point, at approximately 8° of flexion, area contact occurs between all of the arcuate surfaces L and S of the femoral component 12 with all of the arcuate surfaces L and S on the bearing component 16. At this transition point in flexion, contact shifts between surfaces L to surfaces S in a smooth, natural manner because again, as shown in FIG. 3, the arcuate surfaces S and L are tangent to one another at this instant during flexion of the knee. As described previously, this common tangent point is a significant advantage and is a feature that is not shown in any prior art devices. FIG. 3 shows in detail the two radii, R1 which generates the arcuate surface L and R2, which generates the arcuate surfaces. The center of rotation of R2 lies on the radii R1 at point D so that a line tangent to R1 and R2 can be drawn at the point where a line through points C and D intersect the arcuate surface.

It had been suggested in a prior European Patent No. 0,346,183 to Henri Judet, published Dec. 13, 1989, that multiple radii may be advantageous. However, there was no disclosure like the knee herein showing a clear misunderstanding of the requirements for natural knee movement. Judet had no common tangent point at any contact portion between the femoral component and the bearing surface to permit a smooth transition from one surface to the other. The present inventors recognize this important advantage which had never previously been recognized.

The position of the femoral component 12 of FIG. 29 with regard to the bearing element 16 of FIG. 22 is controlled by the center of rotation of curvature for the arcuate surfaces S or L which are in contact. The arcuate surfaces S are placed further back on the bearing and will draw the femoral component posteriorly, thus allowing obligatory rollback. Further rollback is permitted because the elongated aperture 32 in the bearing allows the bearing to move posteriorly on the tibial platform. As described previously, the constraints 26 on the tibial platform and the retaining means 40 prevent anterior movement beyond the interior edge of the tibial platform. Preferably, the lower surface of the bearing element shown in FIG. 22 includes the cutouts 60 defined by the walls 62 and 64 to receive the constraints 26 near the anterior surface of the tibial platform. Therefore, when rollback is occurring during flexion of the knee, no compensatory rollforward will occur between the bearing 16 and the tibial component 14 as the femoral component passes through approximately the 8° range, area contact is transferred between the arcuate surfaces L to the arcuate surfaces S and the transition occurs smoothly because of the common tangent point of the respective arcuate surfaces. The constraints as previously described with respect to the bearing 16 prevent dislocation of the bearing element when implanted.

In the preferred embodiment, as shown in FIGS. 24 and 25, the arcuate surfaces S terminate in a high front wall 120 which provides for a substantially longer, forwardly extended arcuate surface S which provides substantially enhanced posterior stability. This feature will permit the removal of the posterior cruciate ligament, if desired, but it is not required.

The use of two instead of three arcuate surfaces on each condyl portion 20 permits the use of a larger radius in the M-L direction. In contrasting FIG. 5 of the first embodiment with FIG. 29 of the preferred embodiment, it can be seen that the radius R3 which defines the arcuate surface S and the radius R4 which defines the arcuate surface L are larger, therefore providing more contact area for a particular prosthesis. Again, the size of the prosthetic knee of the embodiment shown in FIGS. 22–30 will again vary for each patient. However, the general or approximate dimensions described with respect to the embodiment shown in FIGS. 1–20 will be similar with respect to the embodiment of FIGS. 22–32 except that the radii defining the arcuate surfaces in the transverse plane are substantially larger. The larger radius R3 is particularly advantageous when encountering liftoff as described previously. The larger surface area of the larger arcs provide substantial additional stability.

The knee prosthesis 10 of both embodiments of present invention is the only design which gives area contact between the bearing 16 and the femoral component 12 in all degrees of flexion. The highest pressures on the knee joint are experienced during stair climbing where the knee is flexed to approximately 90 degrees of flexion in which the prior art knees have only line contact or point contact. Since polyethylene (the material used to form the bearing) wear appears to be related to excessive pressures, area contact is more important in stair climbing or rising from a chair than when walking, even though the former may be performed much less often. The prosthetic knee 10 also permits the use of the same component in the presence or absence of posterior cruciate ligaments. Generally speaking, semiconstrained knee prosthesis require the presence of posterior cruciate ligaments to prevent posterior subluxation of the tibia. On the other hand, constrained prosthesis, which do not allow rollback, require removal of the posterior cruciate ligaments because proper tension on the posterior cruciate ligaments would attempt to create posterior rollback which is prevented by the constraints. This could lead to dislocation of the components of the constrained prosthesis or rupture of the posterior cruciate ligaments.

In prior art designs in which the arcuate surfaces of the condyles are created by using a common plane generating curve, all of the sagittal sections of the condyles are polycentric. On the contrary, the present invention has only one radius of contact in each sagittal plane and, therefore, is not created by a common plane generating curve. Since all potential points of contact in the sagittal plane have the same radius of curvature, area contact can be obtained throughout the entire flexion arc of the knee in a manner which cannot be obtained by the prior art knees where the radii along the condyles changes while contacting the same area of the bearing insert.

Referring to FIGS. 18-21, which show the movement of the elements of both embodiments of the prosthetic knee 10 of the present invention implanted in a patient, it can be seen in FIG. 20 that in the extended position of the prosthesis, the bearing insert 16 moves to its anterior-most position with respect to the tibial component 14. In this position, the arcuate surfaces L on the respective tibial component and bearing insert 16 are in engagement. As the knee flexes, rollback of the femur with respect to the tibia begins to occur to approximately the maximum position as shown in FIG. 21 where the bearing insert 16 has moved to its posterior-most position emulating, as close as possible, the normal knee.

Thus, it can be seen that the present invention defines and describes a prosthetic knee which more closely simulates the normal knee movement than any prior art devices. The prosthesis 10 provides normal polycentric motion for the knee joint and permits normal rollback of the femur with respect to the tibia during flexion. The rotational and anterior-posterior movement of the bearing insert is unconstrained for the normal range of motion but is constrained at its limits. The design of the polycentric contact surfaces between the femoral component 12 and the bearing insert 16 assure for sufficient area contact throughout the flexion/extension range of the knee to minimize pressure and resultant wear on the bearing insert.

While it has been found that the design of the prosthetic knee 10 of the present invention as shown and described with respect to FIGS. 22-32 are preferable, the inventors recognize that additional improvements could be made utilizing the common tangent point contact transition feature of the present invention and, therefore, while the foregoing detailed description has been given for clearness and understanding, no unnecessary limitations should be understood therefrom as some modifications will be obvious to those skilled in the art.

We claim:

1. An implantable prosthetic device performing a joint between a pair of human or animal bones, comprising:
   first fixation means adapted for fixation to one of the bones;
   a first bearing surface on said first fixation means, said first bearing surface including at least two, convex, laterally adjacent, arcuate bearing portions of differing radii;
   second fixation means adapted for attachment to the other bone;
   a second bearing surface on said second fixation means, said second bearing surface lying in a plane generally perpendicular to a longitudinal axis of said second fixation means; and
   a bearing element between said first bearing surface and said second bearing surface and having a complementary arcuate surface on one side for engaging the first bearing surface and an opposite surface for engaging said second bearing surface in a predefined range of anterior-posterior sliding engagement and in independently rotatable engagement with said second bearing surface.

2. A prosthetic device as claimed in claim 1 wherein said bearing element is freely rotatable through a predetermined arc in a plane approximately perpendicular to a longitudinal axis of said second fixation means.

3. A prosthetic device as claimed in claim 1 wherein said second bearing surface is a substantially flat surface.

4. A prosthetic device as claimed in claim 1 wherein said second bearing surface is a nearly flat surface of revolution.

5. A prosthetic device as claimed in claim 1, wherein said bearing element is freely movable in a plane approximately perpendicular to a longitudinal axis of said second fixation means.

6. A prosthetic device as claimed in claim 1, wherein said first bearing surface comprises a pair of laterally spaced, arcuate bearing surfaces.

7. A prosthetic knee of claim 1 wherein the first bearing surface has a pair of condylar portions, each condylar portion including two laterally spaced apart condyloid elements, each condyloid element having at least two bearing portions defined by laterally spaced, arcuate segments of different radii.

8. A prosthetic device as claimed in claim 1 wherein said bearing element includes at least two complementary arcuate surfaces on one side for engaging each convex, laterally spaced, arcuate portion of the first bearing surface.

9. A prosthetic device as claimed in claim 1 wherein said arcuate bearing portions of differing radii have a common tangent point.

10. A prosthetic device as claimed in claim 1 wherein the first bearing surface includes a pair of condylar portions, each condylar portion including three laterally spaced arcuate bearing portions of at least two different radii.

11. A prosthetic device for forming a joint between a pair of human or animal bones comprising:
   first fixation means adapted for attachment to one of the bones including a pair of condylar portions;
   a second fixation means adapted for attachment to the other bones including a generally flat bearing surface;
   an intermediate bearing member, said intermediate bearing member mating with said second fixation means such that said intermediate member and said second fixation means bear on one another at a mutually congruent thrust bearing surface of revolution for permitting rotational motion between said intermediate member and said second fixation means while force is transmitted therebetween, and permitting sliding motion of said intermediate member relative to said second fixation means.

12. A prosthetic device as claimed in claim 11 wherein said intermediate member in said congruent thrust bearing relationship with said second fixation means is freely movable in a plane approximately parallel to a plane formed by said flat bearing surface while transmitting force to said second fixation means.

13. A prosthetic device as claimed in claim 12 wherein said mutually congruent thrust bearing surface is a nearly flat surface of revolution whose axis is approximately perpendicular to a plane formed by said flat bearing surface.

14. A prosthetic device as claimed in claim 13 further including stop means for limiting the movement of said congruent thrust bearing.

15. A prosthetic device as claimed in claim 8 wherein each condylar portion includes three arcuate bearing surfaces.

16. A prosthetic device for joining a pair of human or animal bones comprising:
- a first prosthesis having a condylar portion and a fixation portion, said condylar portion including two laterally spaced apart bearing elements, each having at least two arcuate segments of different radii, said fixation portion being adapted to be fixed to one of said bones, said bearing elements being adapted to support weight or be subjected to force while experiencing relative motion;
- a second prosthesis having a bearing surface means for supporting weight and being subjected to force and a fixation portion being adapted to be fixed to the other one of said bones;
- an intermediate load bearing member having a thrust bearing surface means for matingly engaging said bearing surface means and adapted to distribute weight and to transmit forces and to slide through a predefined range of anterior-posterior motion and independently rotate freely in a plane substantially perpendicular to a longitudinal axis of said second prosthesis while distributing weight and transmitting forces thereto, and an upstanding post extending through an aperture in the load bearing member; and
- said mating engagement between said thrust bearing surface means and the arcuate segments being defined by lateral space operable for allowing free mobility.

17. An implantable prosthetic device performing a joint between a pair of human or animal bones, comprising:
- first fixation means adapted for attachment to one of the bones;
- a depending surface on said first fixation means, said depending surface including at least two, convex arcuate bearing surfaces of different radii and having a common tangent point, each bearing surface having an arcuate cross-section in the sagittal plane;
- second fixation means adapted for attachment to the other bone;
- a generally planar bearing surface on said second fixation means; and
- a bearing element between said depending surface and said planar bearing surface, said bearing element having a complementary arcuate surface on one side for engaging the bearing surfaces and an opposite surface for engaging said second bearing surface in a predefined range of anterior-posterior sliding engagement and in independently rotatable engagement with said planar bearing surface.

18. A prosthetic device as claimed in claim 17 wherein said bearing element is freely rotatable through a predetermined arc.

19. A prosthetic device as claimed in claim 17 wherein said bearing element is freely movable in transverse and rotary directions in said plane generally parallel to the planar bearing surface.

20. A prosthetic device of claim 17 wherein the depending surface has a pair of condylar portions, each condylar portion including two laterally spaced condyloid elements each having at least three bearing surfaces defined by laterally spaced, arcuate segments of at least two different radii.

21. An implantable prosthetic device performing a joint between a pair of human or animal bones, comprising:
- first fixation means adapted for attachment to one of the bones;
- a first bearing surface on said first fixation means, said first bearing surface including at least two convex, laterally adjacent, arcuate portions of differing radii;
- second fixation means adapted for attachment to the other bone;
- a second bearing surface on said second fixation means, said second bearing surface lying substantially in a plane;
- a bearing element between said first bearing surface and said second bearing surface and having a complementary arcuate surface on one side for engaging the first bearing surface and an opposite surface in sliding bearing relationship with said second bearing surface; and
- means for connecting said bearing element to said second fixation means such that said bearing element is constrained in its movement relative to said second fixation means along a generally linear path that intersects with and is rotatable about a fixed axis generally perpendicular to said plane of said second bearing.

22. An implantable prosthetic device performing a joint between a pair of human or animal bones, comprising:
- first fixation means adapted for attachment to one of the bones;
- a first bearing surface on said first fixation means;
- second fixation means adapted for attachment to the other bone;
- a second bearing surface on said second fixation means, said second bearing surface lying substantially in a plane;
- a bearing element between said first bearing surface and said second bearing surface and having a complementary arcuate surface on one side for engaging the first bearing surface and an opposite surface in sliding bearing relationship with said second bearing surface; and
- means for connecting said bearing element to said second fixation means such that said bearing element is constrained in its movement relative to said second fixation means along a generally linear path that intersects with and is rotatable about a fixed axis generally perpendicular to said plane of said second bearing.

23. A prosthetic device as claimed in claim 22 wherein said first bearing surface includes at least two, convex, laterally adjacent, arcuate portions of differing radii.

24. A prosthetic device as claimed in claim 22 further comprising stop means for limiting rotational movement of said bearing element relative to said second fixation means, including a pair of protrusions on said second fixation means extending upwardly from said second bearing surface, and a corresponding pair of recesses formed in said bearing element in which said protrusions are respectively received, each of said pair of recesses having an opening on said opposite side of said bearing surface and on an edge of said bearing element intermediate said one side and said opposite side thereof.

25. A prosthetic device as claimed in claim 17 wherein said first bearing surface includes a medial condylar portion and a lateral condylar portion, each of said medial and lateral condylar portions including laterally adjacent convex arcuate portions of differing radii, each of the medially outermost one of said arcuate portions of said medial condylar portion and the laterally outermost one of said arcuate portions of said lateral condylar portion having greater radius than its adjacent arcuate portion, whereby varus/valgus stability of a knee joint throughout its entire range of motion is enhanced.

26. A prosthetic device for joining a pair of human or animal bones comprising:
 a first prosthesis having a condylar portion and a fixation portion, said condylar portion including three laterally spaced apart bearing elements, two of said bearing elements having different radii than the third, said fixation portion being adapted to be fixed to one of said bones, each bearing element being adapted to support weight while experiencing relative motion;
 a second prosthesis having a bearing surface means for supporting weight and being subjected to force and a fixation portion being adapted to be fixed to the other one of said bones;
 an intermediate load bearing member having a thrust bearing surface means for matingly engaging said condylar portion and said bearing surface means and adapted to distribute weight and to slide through a predefined range of anterior-posterior motion and independently rotate freely in a plane substantially parallel to said bearing surface means while distributing weight and transmitting forces thereto; and
 an upstanding post extending through an aperture in the load bearing member.

* * * * *